United States Patent [19]

Lohr, Jr. et al.

[11] 4,060,563

[45] Nov. 29, 1977

[54] PROCESS FOR PREPARING 2-ALLYL PHENOL

[75] Inventors: Delmar Frederick Lohr, Jr., Akron, Ohio; Lynn Burritt Wakefield, Milwaukee, Oreg.

[73] Assignee: The Firestone Tire & Rubber Company, Akron, Ohio

[21] Appl. No.: 733,612

[22] Filed: Oct. 18, 1976

[51] Int. Cl.$^2$ ............................................. C07C 39/20
[52] U.S. Cl. ........................... 260/624 B; 260/621 E; 260/624 E
[58] Field of Search ............ 260/624 B, 624 E, 621 E

[56] References Cited

U.S. PATENT DOCUMENTS 3,198,842  8/1965  Berrigan ............................. 260/624

FOREIGN PATENT DOCUMENTS 700,581  12/1964  Canada ............................. 260/624 B
850,252  10/1960  United Kingdom ............. 260/624 B

*Primary Examiner*—James O. Thomas, Jr.
*Assistant Examiner*—W. B. Lone

[57] ABSTRACT

A process for preparing 2-allyl phenol from phenol comprising an in situ reaction between phenol and an alkali metal hydroxide to form alkali metal phenoxide, adding allyl chloride to said alkali metal phenoxide to form allyl phenyl ether, azeotropically distilling the mixture containing the allyl phenyl ether with an azeotropic solvent to remove various reactant by-products so that only the ether remains and thermally rearranging the allyl phenyl ether to produce 2-allyl phenol.

4 Claims, No Drawings

PROCESS FOR PREPARING 2-ALLYL PHENOL

BACKGROUND OF THE INVENTION

The present invention relates to an improved process for preparing 2-allyl phenol from phenol wherein an azeotropic distillation step is utilized to separate reaction by-products from an intermediate product of allyl phenyl ether which is subsequently thermally rearranged to 2-allyl phenol. More specifically, the present invention relates to an in situ process for preparing an allyl phenyl ether by reacting phenol with an alkali metal hydroxide compound in the presence of a polar solvent, followed by the addition of an azeotropic forming solvent which is added to the mixture and azeotropically distilled to remove various by-products, with the remaining allyl phenyl ether being sufficiently pure to thermally rearrange to 2-allyl phenol.

Heretofore, 2-allyl phenol has generally been obtained from a Claisen rearrangement of allyl phenyl ether which in turn is commonly prepared from the reaction of allyl bromide with sodium phenoxide. However, allyl bromide is fairly expensive in contrast with allyl chloride, generally results in lower yields, and gives a larger amount of by-products. Although various processes have utilized allyl chloride, they generally relate to some complex purification step in which the allyl phenyl ether is removed from the reaction mixture which contains various by-products, solvents, and the like. For example, U.S. Pat. No. 2,968,679 to Aelony, relates to a process for the direct introduction of at least two allyl or methallyl groups onto a ring of a phenol or cresol wherein the reaction is carried out in a substantially anhydrous medium utilizing a non-polar solvent. The resulting product is washed with water, washed with an alkali compound, dried over sodium sulfate, filtered, and fractionated in vacuo.

U.S. Pat. No. 3,198,842 to Berrigan, also relates to a process for the direct introduction of allyl groups. Once again, the reaction is carried out in a polar solvent with the product being separated utilizing known methods, such as separating the allylated phenol from the phenoxide by stripping the solvent and then washing the residue to remove inorganic salts.

Another prior art patent, U.S. Pat. No. 3,526,668 to Starnes and Patton, relates to the method of producing allyl phenols in which an alkali metal salt of a 2,6-disubstituted phenol is contacted in a polar solvent with a primary allyl halide to form the desired product which is substantially free of any ethers. This direct allylation process does not produce any phenol having an allyl group in the ortho position and the recovery of the product is through conventional procedures such as solvent fractionation, solvent precipitation, drying, washing with solvents, fractional distillation, and the like.

Adelson, U.S. Pat. No. 2,605,216 relates to the addition of a third agent or solvent to an azeotropic mixture of allyl alcohol and allyl acetate to form a binary azeotrope which comes off as a distillate with the acetate ester being secured as a residue. Thus, this prior art patent merely relates to a process for separating various solvents or mixtures by separating an already-formed or existing azeotropic solution. It is totally void of any process of forming allyl phenol.

Filar, U.S. Pat. No. 2,862,857, relates to improving an azeotropic distillation process by adding an aqueous alkali metal hydroxide solution to an azeotropic solvent prior to recycling. The desired product, hydroquinone, is distilled with the azeotropic solvent and is separated by crystallizing therefrom or by extracting with water. Thus, once again, the desired compound is obtained by utilizing common and conventional purification techniques. This patent also is void of suggesting any production of an allyl phenol.

SUMMARY OF THE INVENTION

It is therefore an object of the present invention to provide a process for the production of allyl phenol which is inexpensive and gives very good yields.

It is another object of the present invention to provide a process to produce allyl phenol, as above, wherein allyl chloride is utilized.

It is a further object of the present invention to provide a process to produce allyl phenol, as above, wherein an allyl phenyl ether intermediate is produced using a slight excess of an alkali metal hydroxide.

It is an additional object of the present invention to provide a process for producing allyl phenol, as above, wherein said ether intermediate is produced in situ and in the presence of a polar solvent.

It is still another object of the present invention to produce allyl phenol, as above, wherein an azeotropic-forming solvent is added to said ether intermediate so that upon azeotropic distillation, all of the various by-products as well as the azeotropic-forming solvent is removed, thereby leaving a pure allyl phenyl ether intermediate which is readily, thermally rearranged to 2-allyl phenol.

GENERAL DESCRIPTION OF THE INVENTION

Generally, the process for preparing 2-allyl phenol from phenol comprises the steps of, reacting in situ a compound selected from the class consisting of an alkali metal hydroxide with the phenol to form an alkali phenoxide, reacting said alkali phenoxide with allyl chloride to form an allyl phenyl ether mixture containing various by-products, adding a non-polar hydrocarbon solvent selected from the class consisting of an aliphatic having from 6 to 12 carbon atoms, a cycloaliphatic having from 6 to 12 carbon atoms, an aromatic having from 6 to 12 carbon atoms, and combinations thereof, azeotropically distilling off said non-polar hydrocarbon solvents and said various reaction by-products so that only said allyl phenyl ether remains, and thermally rearranging said allyl phenyl ether to produce 2-allyl phenol.

DESCRIPTION OF THE PREFERRED EMBODIMENTS

According to the concepts of the present invention, allyl chloride is reacted with an alkali phenoxide to produce allyl phenyl ether as an intermediate along with various by-products. In order to remove the by-products, a non-polar hydrocarbon solvent is added so that an azeotrope is produced upon distillation of the various by-products so that substantially pure allyl phenyl ether remains. The ether is then thermally rearranged to produce 2-allyl phenol.

Phenol is added to a vessel or other container which is then charged with a slight excess of an alkali metal hydroxide to produce an in situ reaction yielding an alkali metal phenoxide. Generally, the reaction is carried out at ambient temperatures and in the presence of a polar solvent. Usually, the phenol is dissolved in the polar solvent which may be any water miscible compound. The alcohols and diols constitute such a desirable compound and include alcohols having from 1 to 6 carbon atoms. Specific examples include methyl alcohol, ethyl alcohol, propyl alcohol, isopropyl alcohol, butyl alcohol and the isomers thereof, amyl alcohol and the various isomers thereof, hexyl alcohol and the various isomers thereof, and the like. Allyl alcohol may also be utilized. The diols generally have from 2 to 4 carbon atoms and specific examples include ethylene glycol, propylene glycol, trimethylene glycol, and the like. A highly preferred solvent is isopropanol (isopropyl alcohol). Usually, the phenol is dissolved in the polar solvent and added to the vessel. The amount of the alkali metal hydroxide compound generally ranges from 1.0 to about 1.5 equivalence based upon the phenol with a range of from 1.0 to about 1.2 being preferred. The alkali hydroxide is generally added in concentrated form dissolved in water, with potassium hydroxide being desirable, and with sodium hydroxide being highly preferred. The vessel or container usually has an inert atmosphere such as nitrogen during the addition of the alkali hydroxide and it is usually advantageous to use cooling. The formation of the alkali phenoxide usually occurs immediately.

Allyl chloride is added or charged to the vessel and heated with the reaction taking place under autogenous pressure to produce the allyl phenyl ether and an alkali metal chloride salt. A slight excess of the allyl chloride is desirable based upon the amount of the alkali phenoxide and may range from about 1.1 to about 1.5 equivalents. The temperature of the reaction is kept below the boiling point of the alcohol or the diol, that is the polar solvent, and desirably is from about 20° C to about 100° C with a preferred temperature range being from about 60° C to about 80° C. Sometimes the vessel may be initially charged under a slight pressure such as about 70kPa. The reaction, which is generally agitated, is continued until completed and usually involves a period of a few hours.

The reaction mixture containing the allyl phenyl ether is then washed with a suitable compound such as water to remove the polar solvent, any unreacted alkali phenoxide, and the produced alkali chloride salt. The reaction mixture is usually washed a plurality of times so that only a very small amount of these by-products remain.

An azeotropic-forming, non-polar, hydrocarbon solvent is then added to the vessel and heated so that the various remaining reaction by-products are azeotropically distilled whereby substantially pure allyl phenyl ether remains in the vessel. It has been found that if this azeotropic step is omitted prior to the thermal rearrangement and/or, for example, routine distillation is utilized, only resinous products are obtained. Should the azeotropic-forming solvent be added prior to the ether formation step, then small amounts of ether is obtained. The non-polar hydrocarbon solvent generally has from 6 to 12 carbon atoms and may be an aliphatic compound, a cycloaliphatic compound, an aromatic compound, and combinations thereof. The non-polar solvent further has a boiling point of about 70° C to about 140° C with a boiling point of 80° C to about 110° C being preferred. Specific examples of aliphatic solvents include hexane, heptane, octane, heptene, and octene. Examples of cycloaliphatics include cyclohexane, cycloheptane, cyclohexene, cycloheptene, and the like. Additionally, various alkyl substituted cyclohexanes may be utilized which have a boiling point between 70° C and 140° C. Examples of suitable aromatic compounds or aliphatic substituted aromatic compounds include benzene, toluene, the various xylene isomers, ethylbenzene, and the like. It has been found that benzene produces desirable results and that toluene is highly preferred.

The non-polar hydrocarbon solvent such as toluene will form an azeotrope upon distillation with any of the reaction by-products or impurities. The impurities, usually remaining after washing as small amounts or as traces, are allyl chloride, water, and the polar solvent such as isopropanol. Upon the addition of azeotropic-forming solvent, the reaction vessel is heated to a temperature just below the boiling point of the azeotropic solvent, that is to a temperature at which the azeotrope forms. Usually, this is a few degrees below the boiling point of the non-polar azeotropic solvent. The reaction, of course, is continued until all of the solvent has been removed. Generally, the amount of the solvent may vary and may, for example, be equal to the volume of the original reaction mixture volume prior to the in situ reaction so that the reaction volume contains a volume similar to the ether formation step. Of course, larger or smaller amounts may be utilized since the only important requirement is that a sufficient amount of solvent be utilized to form an azeotropic system. This amount will vary with the amount of remaining impurities or by-products, but generally is very small such as a volume of about 4.0 times the volume of the impurities. Of course, the maximum amount of solvent is limited only by practical considerations such as the volume size of the reaction vessel, desirable azeotropic distillation time, and the like.

After azeotropic distillation, the remaining, substantially pure allyl phenyl ether is thermally rearranged by heating to produce 2-allyl phenol. The heating temperature may range from about 160° C to about 240° C with a more desirable range being from 190° C to about 220° C. A preferred range extends from about 200° C to about 220° C. The time, of course, will vary depending upon the temperature, and generally a few to several hours of rearrangement time is involved.

Yields of from about 85 percent to about 95 percent are easily obtained according to the present process.

The product 2-allyl phenol may be utilized for introducing cross-linking sites into polyphosphazene compounds.

The invention will be better understood by reference to the following examples.

EXAMPLES I – IV

To a reaction bottle was added 8.0 moles of phenol (753 grams) dissolved in 1,200ml of isopropanol. To this was added 8.0 moles of sodium hydroxide (320 grams) dissolved in 300ml of water. The bottle was rinsed three times by adding each time 200ml of isopropanol with reaction of the sodium hydroxide and phenol occurring immediately. Allyl chloride, in an amount of 9.6 moles, was charged. The mixture was then agitated and heated. A slight nitrogen pressure of approximately 70 kPa (10 psig) was placed on the reaction bottle. The reactor was brought up to a temperature of approximately 70° C. After approximately 5 hours at 70° C, the formation of allyl phenyl ether was judged complete and the reaction bottle was allowed to come to room temperature. The reaction mixture was then washed twice with 3 liters of water to remove sodium chloride, isopropanol, and unreacted sodium phenoxide as well as other by-products. The bottle was then charged with 3 liters of toluene, mixed, and heated to a temperature of approximately 100° C. An azeotropic distillation occured and was continued for approximately 3 hours during which time the toluene was distilled off along with traces of water, isopropanol, unreacted allyl chloride, and other by-products. The remaining allyl phenyl ether was sufficiently pure to be thermally rearranged to 2-allyl phenol. The rearrangement process occurred at 200° C and continued for approximately 5 hours. After this time, the reaction was stopped and a gas chromatographic analysis of the product was made. A 2-allyl phenol yield of 90.6 percent was achieved.

Two further samples of 2-allyl phenol were prepared in an identical manner as set forth above. In Example II, the yield of 2-allyl phenol was 89.6. In Example III, a yield of 95.0 percent was achieved.

In comparison, the above procedure was repeated (Example IV) except that the azeotropic drying step was omitted. Gas chromatographic analyses revealed a 2-allyl phenol content of 64.2 percent. However, upon conventional distillation, the 2-allyl phenol could not be separated and only a viscous tar was obtained.

Thus, according to the above examples and data, it can readily be seen that very high yields of 2-allyl phenol are easily obtained.

While in accordance with the patent statutes, preferred embodiments have been illustrated and described in detail, it is to be understood that the invention is not limited thereto, the scope of the invention being measured by the scope of the appended claims.

What is claimed is:

1. A process for preparing 2-allyl phenol from phenol comprising, the sequential steps of:
   a. reacting in situ a compound selected from the class consisting of an alkali metal hydroxide with the phenol to form an alkali phenoxide, the amount of said alkali metal hydroxide to said phenol ranging from about 1.0 to about 1.5 on an equivalent basis,
   b. carrying out said in situ reaction in a water miscible polar solvent, said polar solvent selected from the class consisting of alcohols having from 1 to about 6 carbon atoms and diols having from 2 to about 4 carbon atoms,
   c. reacting said alkali phenoxide with allyl chloride in said polar solvent to form an allyl phenyl ether mixture containing various by-products,
   d. reacting said alkali metal phenoxide with said allyl chloride under autogenous pressure at a temperature of from about 20° C to about 100° C, the amount of said allyl chloride to said alkali phenoxide ranging from about 1.1 to about 1.5 equivalents,
   e. washing said allyl phenyl ether mixture with water,
   f. adding to said allyl phenyl ether mixture a non-polar hydrocarbon azeotropic solvent, said non-polar solvent being an aromatic having from 6 to 12 carbon atoms,
   g. azeotropically distilling off said non-polar hydrocarbon solvent and said various reaction by-products so that only said allyl phenyl ether remains, said azeotropically distillation occurring at a temperature slightly below the boiling point of said azeotropic non-polar solvent, the boiling point of said azeotropic non-polar solvent ranging from about 70° C to about 140° C, and
   h. thermally rearranging said allyl phenyl ether to produce 2-allyl phenol, said rearrangement occurring at a temperature of from about 160° C to about 240° C.

2. A process according to claim 1, wherein said azeotropic solvent is selected from the class consisting of benzene, toluene, the various isomers of xylene, and ethylbenzene.

3. A process according to claim 2, wherein said alkali metal hydroxide is selected from the group consisting of potassium hydroxide and sodium hydroxide, said azeotropic solvent is selected from the group consisting of benzene and toluene and said polar solvent is isopropanol.

4. A process according to claim 3, wherein said alkali metal hydroxide is sodium hydroxide so that sodium phenoxide is formed, the amount of said sodium hydroxide to said phenol ranging from about 1.0 to about 1.2 equivalents, reacting said sodium phenoxide with said allyl chloride at a temperature of about 60° C to about 80° C, said azeotropic solvent is toluene, and said thermal rearrangement is carried out at a temperature of from about 190° C to about 220° C.

* * * * *